(12) United States Patent
Bradley

(10) Patent No.: US 7,127,296 B2
(45) Date of Patent: Oct. 24, 2006

(54) METHOD FOR INCREASING THE THERAPEUTIC RATIO/USAGE RANGE IN A NEUROSTIMULATOR

(75) Inventor: Kerry Bradley, Glendale, CA (US)

(73) Assignee: Advanced Bionics Corporation, Valencia, CA (US)

( * ) Notice: Subject to any disclaimer, the term of this patent is extended or adjusted under 35 U.S.C. 154(b) by 642 days.

(21) Appl. No.: 10/285,817

(22) Filed: Nov. 1, 2002

(65) Prior Publication Data
US 2003/0093134 A1    May 15, 2003

Related U.S. Application Data

(60) Provisional application No. 60/336,451, filed on Nov. 2, 2001.

(51) Int. Cl.
*A61N 1/20* (2006.01)
(52) U.S. Cl. ........................................... 607/46
(58) Field of Classification Search .................. 607/43, 607/46, 55–57, 62–63
See application file for complete search history.

(56) References Cited

U.S. PATENT DOCUMENTS

| | | | |
|---|---|---|---|
| 3,646,940 A | | 3/1972 | Timm et al. |
| 3,724,467 A | | 4/1973 | Avery et al. |
| 3,822,708 A | | 7/1974 | Zilber |
| 4,459,989 A | | 7/1984 | Borkan |
| 5,342,409 A | * | 8/1994 | Mullett ........................ 607/46 |
| 5,443,486 A | * | 8/1995 | Hrdlicka et al. .............. 607/59 |
| 5,626,629 A | | 5/1997 | Faltys et al. |
| 5,643,330 A | | 7/1997 | Holsheimer et al. |
| 5,653,739 A | * | 8/1997 | Maurer et al. ................ 607/46 |
| 5,776,170 A | * | 7/1998 | MacDonald et al. .......... 607/46 |
| 5,814,082 A | * | 9/1998 | Fayram et al. ................ 607/5 |
| 5,873,900 A | * | 2/1999 | Maurer et al. ................ 607/46 |
| 5,925,070 A | * | 7/1999 | King et al. .................... 607/67 |
| 5,938,690 A | | 8/1999 | Law et al. |
| 6,157,861 A | * | 12/2000 | Faltys et al. .................. 607/57 |
| 6,393,325 B1 | | 5/2002 | Mann et al. |

(Continued)

FOREIGN PATENT DOCUMENTS

WO    WO 02/09808    2/2002

OTHER PUBLICATIONS

Meadows; U.S. Appl. No. 09/718,648 filed, Nov. 21, 2000 entitled "Externally-Controllable Constant-Flow Medication Delivery System".

(Continued)

*Primary Examiner*—George Manuel
(74) *Attorney, Agent, or Firm*—Henricks, Slavin & Holmes LLP

(57) ABSTRACT

A system and method for patient control of the stimulation parameters of a Spinal Cord Stimulation (SCS) system, or other neurostimulation system, provides an increased Therapeutic Ratio (TR). Measurements of the just-perceptible stimulation level and the maximum-comfortable stimulation level are made for at least two values of pulse duration and two values of pulse amplitude. A Therapeutic Ratio is determined for stimulation level control strategies based on fixed pulse duration and variable pulse amplitude, and alternatively for fixed pulse amplitude and variable pulse duration. The control strategy providing the greatest therapeutic ratio is then selected for use by the patient. In an alternative embodiment, the pulse durations at the just-perceptible and maximum-comfortable stimulation levels are measured, and the pulse amplitudes at the just-perceptible and maximum-comfortable stimulation levels are determined using a curve-fitting process. Similarly, the pulse amplitudes may first be measured and the pulse widths determined using a curve-fitting process.

16 Claims, 5 Drawing Sheets

U.S. PATENT DOCUMENTS 6,516,227 B1   2/2003   Meadows et al.
6,546,290 B1   4/2003   Shloznikov
6,587,724 B1   7/2003   Mann
6,622,048 B1   9/2003   Mann et al.

OTHER PUBLICATIONS

Mann; U.S. Appl. No. 09/740,3389, filed Dec. 18, 2000 entitled "Magnitude Programming for Implantable Electrical Stimulator".

* cited by examiner

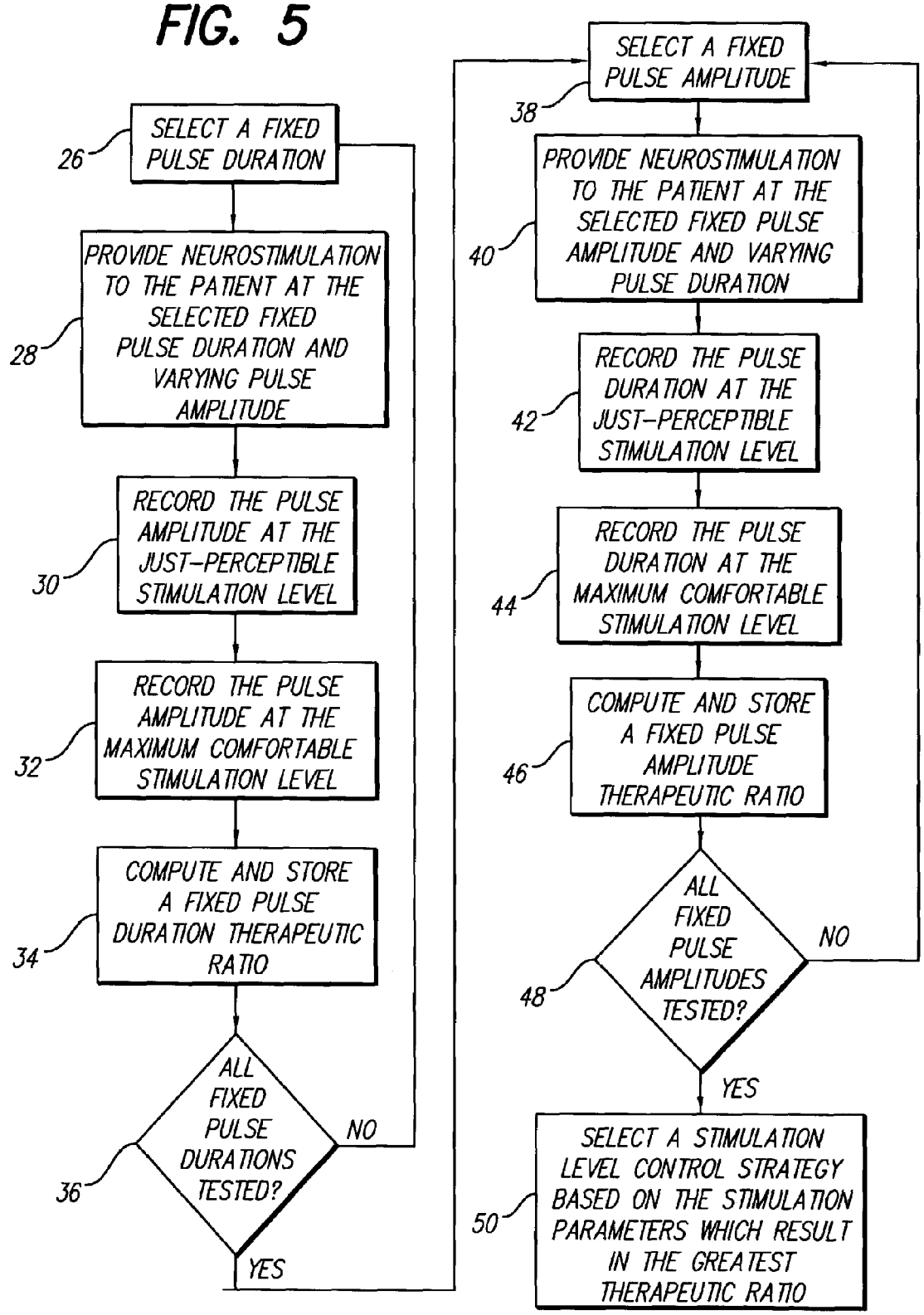

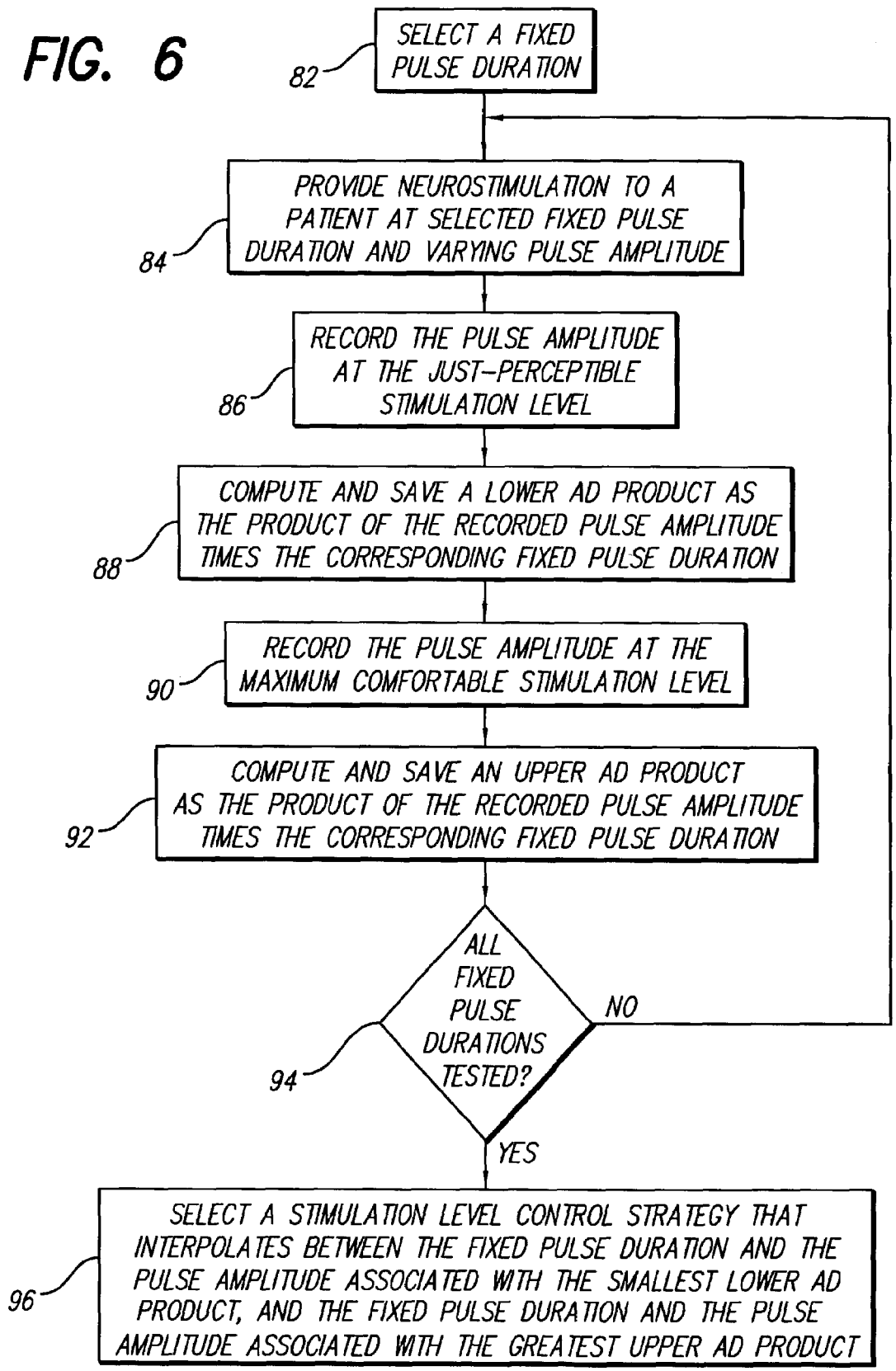

METHOD FOR INCREASING THE THERAPEUTIC RATIO/USAGE RANGE IN A NEUROSTIMULATOR

The present application claims the benefit of U.S. Provisional Application Ser. No. 60/336,451, filed Nov. 2, 2001, which application is incorporated herein by reference.

BACKGROUND OF THE INVENTION

The present invention relates to neurostimulation systems (for example, a Spinal Cord Stimulation (SCS) system), and more particularly to a system and method for increasing the therapeutic ratio and usage range in a neurostimulator.

A spinal cord stimulation system treats chronic pain by providing electrical stimulation pulses through the electrodes of an electrode array placed epidurally near a patient's spinal cord. The therapeutic ratio is defined as the ratio of the maximum comfortable stimulation amplitude (numerator) to the just-perceivable stimulation amplitude (denominator). The therapeutic ratio is important because it is a measure of the range of adjustment allowed to a patient to meet varied pain relief/paresthesia requirements during the patient's daily activities. A large therapeutic ratio provides tolerance for changes in a patient's activities of daily living (posture variations, etc.) that may affect stimulation effectiveness. A low therapeutic ratio does not provide much tolerance for changes in the patient's activities.

Spinal cord stimulation is a well accepted clinical method for reducing pain in certain populations of patients. SCS systems typically include an Implantable Pulse Generator (IPG), electrodes positioned on an electrode lead, and (in some instances) an electrode lead extension. The IPG generates electrical pulses that are delivered to the dorsal column fibers and dorsal root fibers in the spinal cord, through the electrodes. The electrodes are implanted along the dura of the spinal cord. Individual electrode contacts (the "electrodes") may be arranged in a desired pattern and spacing in order to create an electrode array. Individual wires connect with each electrode in the array. These wires are encased within an insulating material, and thus incased are generally referred to as a lead. Typically, the lead exits the spinal column and attaches to an electrode lead extension. The electrode lead extension, in turn, is typically tunneled around the torso of the patient to a subcutaneous pocket where the IPG is implanted. (In some instances, the lead that exits the spinal column may be connected directly to the IPG.)

SCS and other stimulation systems are known in the art. For example, an implantable electronic stimulator is disclosed in U.S. Pat. No. 3,646,940, that provides timed sequenced electrical impulses to a plurality of electrodes. As another example, U.S. Pat. No. 3,724,467 teaches an electrode implant for neuro-stimulation of the spinal cord. A relatively thin and flexible strip of biocompatible material is provided as a carrier on which a plurality of electrodes are formed. The electrodes are connected by a conductor, e.g., a lead body, to an RF receiver, which is also implanted, and which is controlled by an external controller.

In U.S. Pat. No. 3,822,708, another type of electrical spinal cord stimulation device is taught. The device disclosed in the '708 patent has five aligned electrodes which are positioned longitudinally on the spinal cord. Current pulses applied to the electrodes block sensed intractable pain, while allowing passage of other sensations. The stimulation pulses applied to the electrodes have a repetition rate of from 5 to 200 pulses per second. A patient operated switch allows the patient to change which electrodes are activated, i.e., which electrodes receive the stimulation pulses, so that the region between the activated electrodes on the spinal cord can be adjusted, as required, to better block the pain.

When an SCS system is implanted, a fitting procedure is performed to optimize the stimulation parameters for the particular patient. The stimulation parameters are optimized for both treatment efficacy, and to minimize power consumption. Disadvantageously, following optimization, the stimulation pulse width is generally fixed at some nominal value, and the patient is limited to control of the stimulation amplitude. Typically, such limited control has been shown to result in a therapeutic ratio of only about 1.4. As a result of such small therapeutic ratio, the patient must be careful to not adjust the stimulation level too abruptly or inadvertent over-stimulation may result. Also, if the patient's pain increases, such small therapeutic ratio may result in the patient exceeding the maximum comfortable amplitude to obtain pain relief.

What is needed is a method to increase the therapeutic ratio in order to provide more effective pain relief.

SUMMARY OF THE INVENTION

The present invention addresses the above and other needs by providing a method for patient control of the stimulation parameters of a Spinal Cord Stimulation (SCS) system, or other neural stimulation system, that allows an increased Therapeutic Ratio (TR) to be achieved. As has been indicated, the Therapeutic Ratio is defined as the ratio of the maximum comfortable stimulation magnitude (numerator) to the just-perceivable stimulation magnitude (denominator). The magnitude of the stimulation level may be measured in terms of stimulation pulse amplitude or stimulation pulse duration. The therapeutic ratio is important because it is a measure of the range of adjustment allowed to a patient to meet varied pain relief/paresthesia requirements during the patient's daily activities. A large therapeutic ratio provides tolerance for changes in a patient's activities of daily living (posture variations, etc.) that may affect stimulation effectiveness. A low therapeutic ratio does not provide much tolerance for changes in the patient's activities.

In accordance with one aspect of the invention, measurements based on the patient's perception of the just-perceptible stimulation level and the maximum comfortable stimulation level are made for at least two values of pulse duration and two values of pulse amplitude. The therapeutic ratio is determined for stimulation level control strategies based on fixed pulse duration and variable pulse amplitude, and alternatively, upon fixed pulse amplitude and variable pulse duration. The stimulation level control strategy, where "stimulation level control strategy" comprises that combination of stimulation pulse amplitudes and stimulation pulse widths used by the neurostimulation device, that provides the greatest therapeutic ratio is then selected for use by the patient. In an alternative embodiment, the just-perceptible stimulation levels, and the maximum comfortable stimulation levels, are determined for a range of pulse durations and pulse amplitudes. The product of pulse amplitude times pulse duration is computed (the "AD product") for each level, and a stimulation level trajectory is determined running from the just-perceptible stimulation level with the smallest AD product, to the maximum comfortable stimulation level with the greatest AD product, with the pulse amplitude and pulse duration changing gradually along the trajectory.

In accordance with another aspect of the invention, there is provided a method for comparing the therapeutic ratio (TR) resulting from a fixed pulse duration and from a fixed pulse amplitude. The stimulation control strategy providing the greatest TR is selected for use by the patient. As a result, the patient has the broadest available control over stimulation level, and the sensitivity of pain management to small changes in, for example, the patient's posture, are minimized.

It is a feature of the present invention to provide a multiplicity of embodiments of the method to increase the therapeutic range of a neurostimulator. A clinician may exercise one or more of the embodiments, and select the embodiment that provides the best results for each individual patient.

It is a further feature of the invention to select between two stimulation control strategies resulting in similar TRs by selecting the strategy with the lowest power consumption. Many known neural stimulator systems comprise battery powered fully-implantable devices. Such devices may require surgery to remove spent batteries, and therefore battery life is a major issue. By selecting the strategy that results in lower power consumption, the time between surgical battery replacements is increased.

BRIEF DESCRIPTION OF THE DRAWINGS

The above and other aspects, features and advantages of the present invention will be more apparent from the following more particular description thereof, presented in conjunction with the following drawings wherein:

FIG. 5 shows a flow chart for a first embodiment of a method for selecting a stimulation control strategy which results in an increased therapeutic ratio; and FIG. 6 shows a flow chart for a second embodiment of a method for selecting a stimulation control strategy which results in an increased therapeutic ratio.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The method for increasing the Therapeutic Ratio (TR) of a neurostimulation system in accordance with the present invention provides a stimulation control strategy for neurostimulation systems, e.g., a Spinal Cord Stimulation (SCS) system, which compares alternative control strategies, and selects the strategy that results in the highest Therapeutic Ratio. If two or more alternative control strategies provide similar Therapeutic Ratios, then the control strategy with the lowest power consumption is selected.

Figures 1, 2:
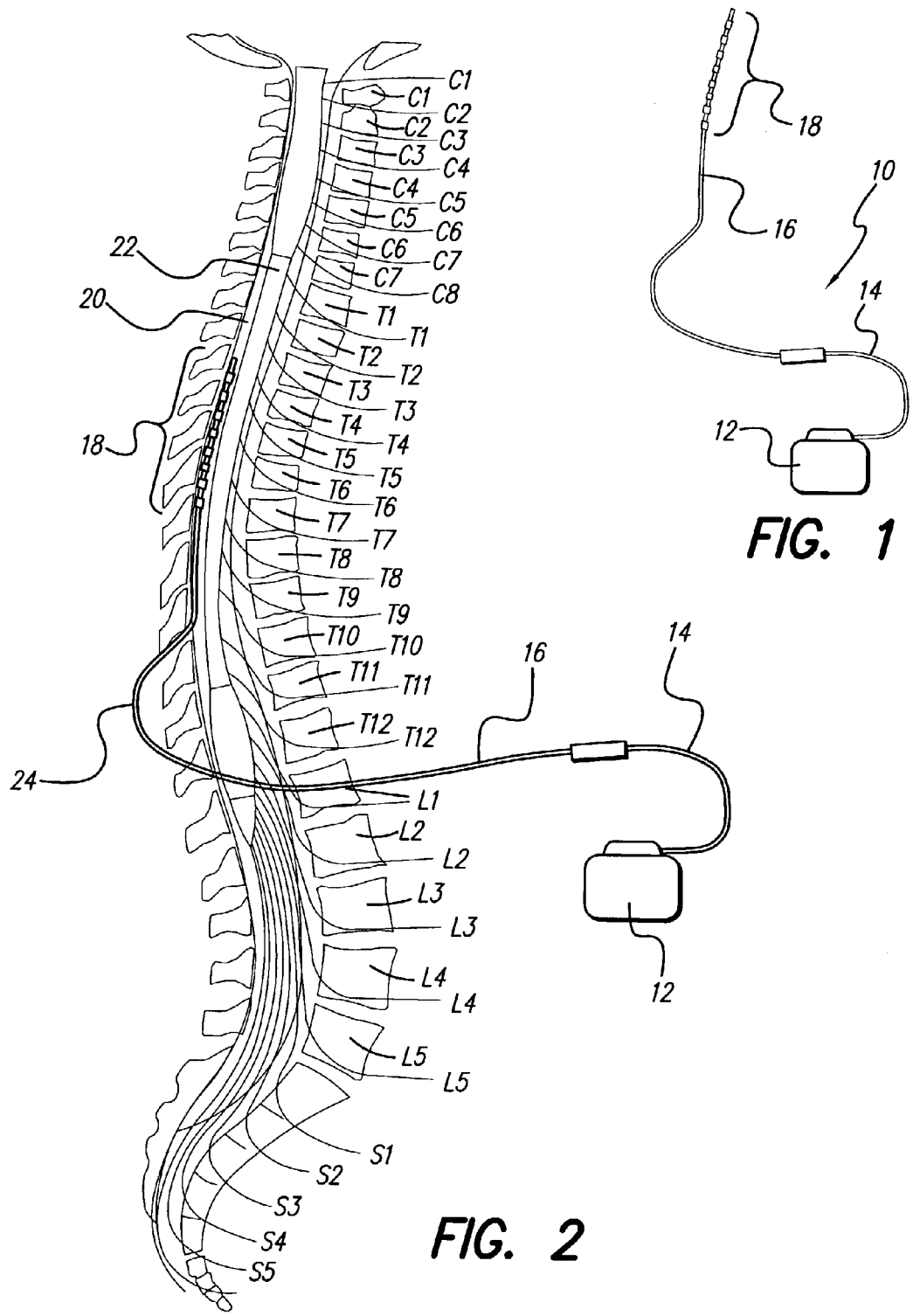
FIG. 1 shows a Spinal Cord Stimulation (SCS) system.
FIG. 2 depicts an SCS system implanted in a patient.

A Spinal Cord Stimulation system 10, as shown in FIG. 1, typically comprises an Implantable Pulse Generator (IPG) 12, a lead extension 14, an electrode lead 16, and an epidural electrode array 18. The IPG 12 generates stimulation current for implanted electrodes that make up the epidural electrode array 18. A proximal end of the lead extension 14 is detachably connected to the IPG 12, and a distal end of the lead extension 14 is detachably connected to a proximal end of the electrode lead 16. The epidural electrode array 18 is formed on or near a distal end of the electrode lead 16. The in-series combination of the lead extension 14 and electrode lead 16 carry the stimulation current from the IPG 12 to the individual electrodes of the epidural electrode array 18. The epidural electrode array 18 is typically formed from a series of ring electrodes, and is sometimes referred to as a ring electrode array.

The SCS system 10 of FIG. 1 is shown implanted in the epidural space 20 of a patient in FIG. 2. The epidural electrode array 18 is implanted at the site of nerves that are the target of stimulation (e.g., against the spinal cord 22). Due to the lack of space near the lead exit point 24 where the electrode lead 16 exits the spinal column, the IPG 12 is generally implanted in the abdomen or above the buttocks. The lead extension 14 facilitates locating the IPG 12 away from the lead exit point 24.

While the implantable system depicted in FIGS. 1 and 2 includes a separate lead extension 14 and electrode lead 16 connecting the IPG 12 to the epidural electrode array 18, the present invention would also apply equally well to an SCS system with a single lead connecting the IPG 12 to the epidural electrode array 18. Also, other electrode arrays are known in the art, and an SCS, or other neurostimulation system, using a different type of electrode array may be used with the present invention.

A representative SCS system with which the present invention may be used, including a description of different types of electrode arrays that may be used as part of such SCS system, is described more fully in U.S. patent application Ser. No. 09/626,010, filed Jul. 26, 2000, now U.S. Pat. No. 6,516,227, which patent application is assigned to the same assignee as is the present application, and which patent application is incorporated herein by reference. See also International Publication Number WO 02/09808 A1, published Feb. 7, 2002, based on International Application Number PCT/US00/20294, filed Jul. 26, 2000, also incorporated herein by reference.

Known neurostimulation systems, including the SCS system described in the above-referenced U.S. Pat. No. 6,516,227, have the ability to vary a set of stimulation parameters to tune the stimulation to the pain being targeted, and to control the overall stimulation level. See also, e.g., U.S. Pat. No. 6,393,325, incorporated herein by reference, and U.S. patent applications Ser. No. 09/718,648, filed Nov. 21, 2000, now U.S. Pat. No. 6,622,048; and Ser. No, 09/740,339, filed Dec. 18, 2000, now U.S. Pat. No. 6,587,724, all assigned to the same assignee as is the present application, and each of which is also incorporated herein by reference. Stimulation parameters that may be adjusted to control the overall stimulation level include: pulse amplitude, pulse duration (also referred to as pulse width), and pulse frequency (the repetition rate for the pulses.)

Generally, the overall stimulation level control is achieved by varying the pulse amplitude. In accordance with the present invention, a fitting process is performed during which the pulse duration (pulse width) is set to a fixed pulse duration (width), and the pulse amplitude is then varied to determine the pulse amplitude at the just-perceptible stimulation level, and the pulse repeated at the maximum comfortable stimulation level. This process is then repeated for other fixed pulse durations (widths).

Figure 3:
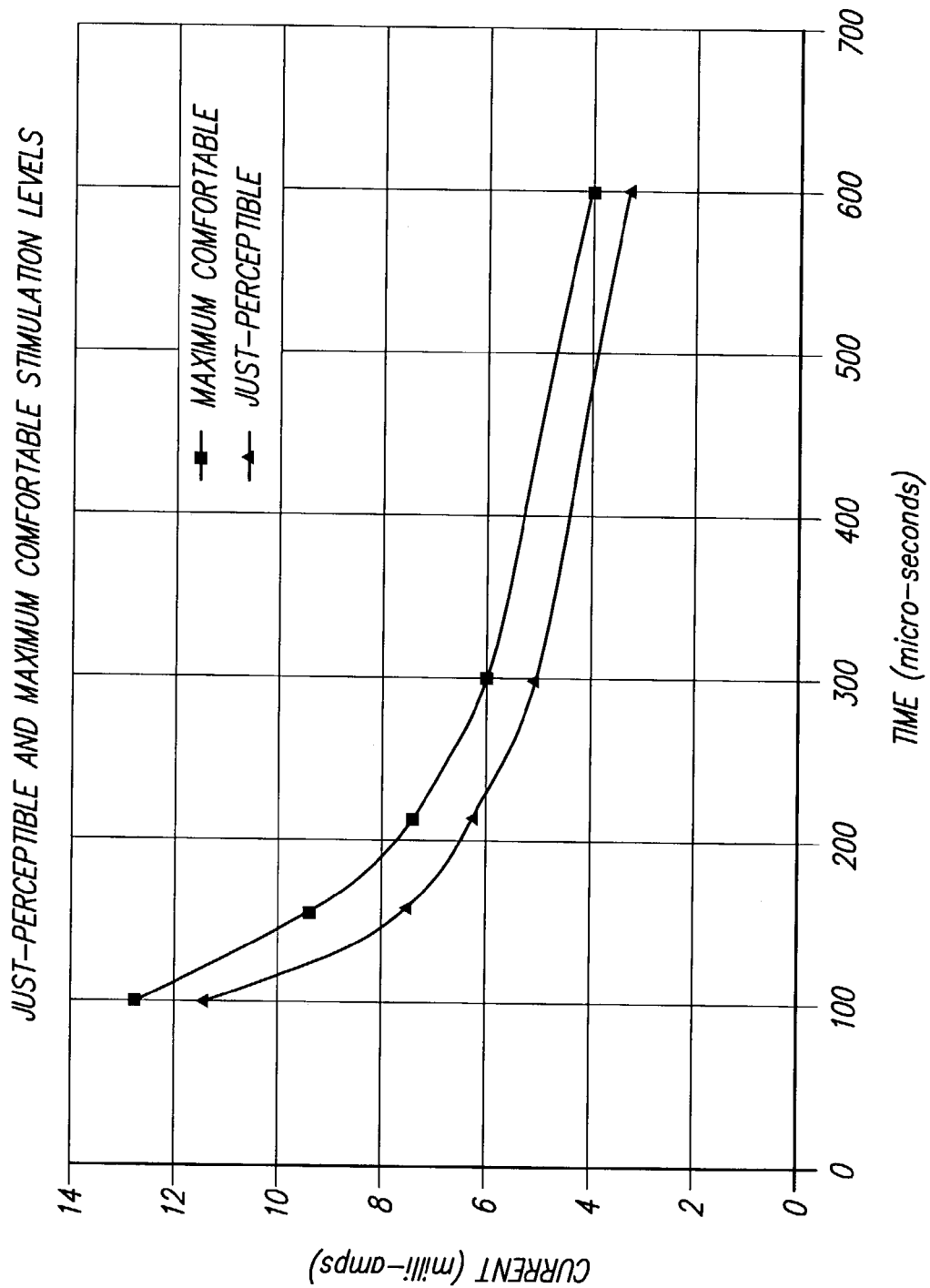
FIG. 3 depicts a plot of the just-perceptible stimulation level and the maximum comfortable stimulation level, wherein the axes are the pulse duration in microseconds and the pulse amplitude in milliamps.

The data resulting from five fixed pulse durations (pulse widths) are plotted in FIG. 3 and tabulated in Table 1. In FIG. 3, the horizontal axis is time (microseconds) and the vertical axis is amplitude, expressed in milliamps. The various pulse durations (pulse widths), expressed in microseconds, and corresponding pulse amplitudes, expressed in milliamps, that provide the maximum comfortable level (plotted as small square dots), and the just perceptible level (plotted as small triangular dots), are shown in FIG. 3. As seen in FIG. 3, such data show that the narrower the pulse width, the higher the pulse amplitude must be to achieve a desired stimulation level. Similarly, the data show that the wider the pulse width, the lower the pulse amplitude may be to achieve the same desired stimulation level.

TABLE 1

Fixed Pulse Duration Data

| Pulse Duration (microseconds) | Just-Perceptible Stimulation Level (milliamps) | Maximum Comfortable Stimulation Level (milliamps) | Therapeutic Ratio TR |
|---|---|---|---|
| 100 | 11.6 | 12.7 | 1.09 |
| 150 | 7.6 | 9.3 | 1.22 |
| 210 | 6.3 | 7.3 | 1.16 |
| 300 | 5.0 | 6.0 | 1.20 |
| 600 | 3.4 | 4.0 | 1.18 |

For the example depicted in FIG. 3, the Therapeutic Ratio (TR) resulting from each process is tabulated in the fourth column of Table 1. The greatest therapeutic ratio, 1.22, was obtained using a pulse duration of 150 microseconds.

While known systems rely upon a process limited to a fixed pulse duration stimulation level control strategy, the method of the present invention expands the process to include a fixed pulse amplitude stimulation level control strategy.

Figure 4:
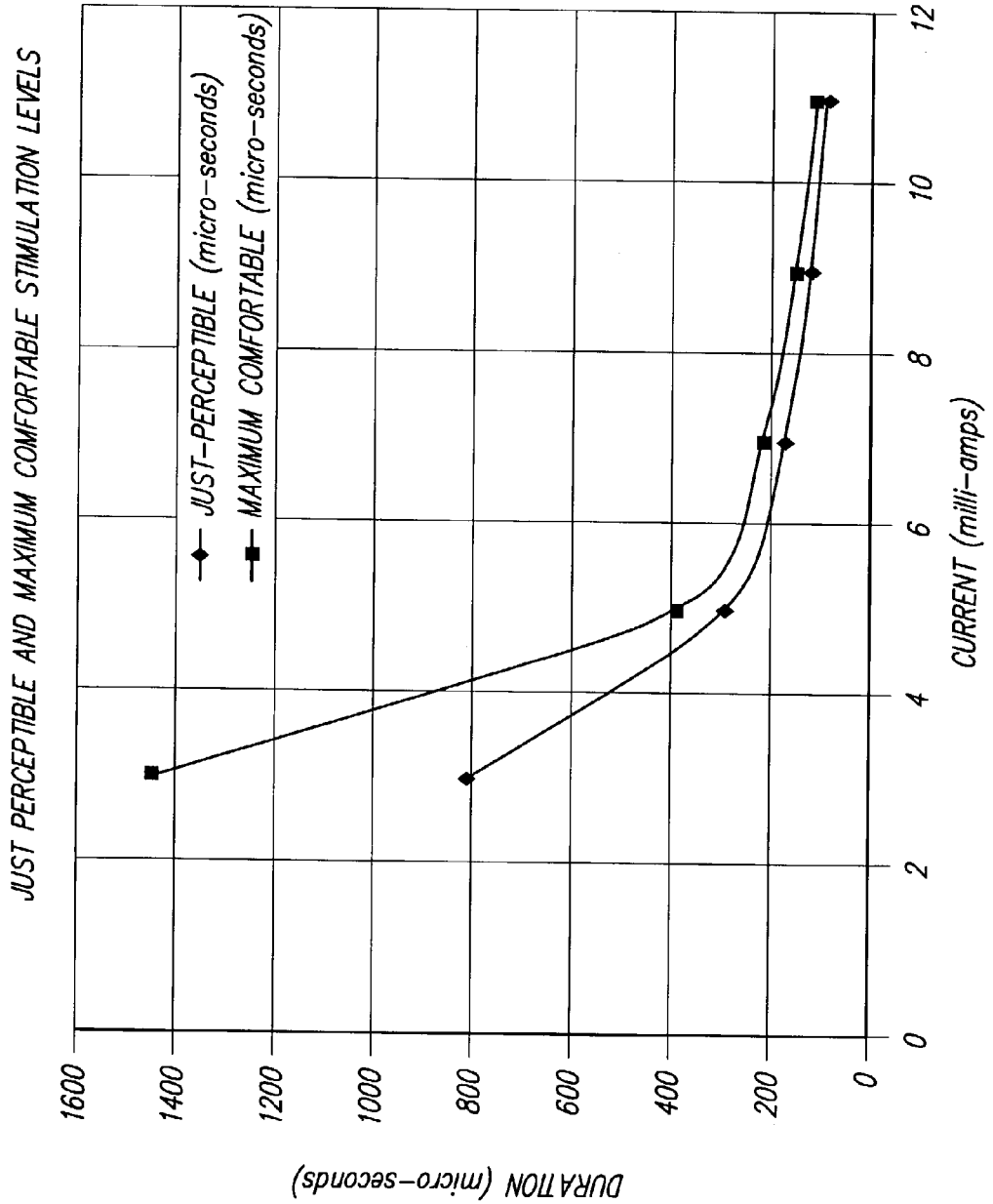
FIG. 4 depicts a plot similar to FIG. 3, but with duration in micro-seconds replacing current in milliamps as the vertical axis.

A second phase of the fitting process is performed during which the pulse amplitude is set to a fixed pulse amplitude, and the pulse duration is varied to determine the pulse duration at the just-perceptible stimulation level, and the pulse duration at the maximum comfortable stimulation level. The second phase is then repeated for other fixed pulse amplitudes. Data resulting from five fixed pulse amplitudes are plotted in FIG. 4 and tabulated in Table 2.

TABLE 2

Fixed Pulse Amplitude Data

| Pulse Amplitude (milliamps) | Just-Perceptible Stimulation Level (microseconds) | Maximum Comfortable Stimulation Level (microseconds) | Therapeutic Ratio (TR) |
|---|---|---|---|
| 3 | 810.07 | 1437.29 | 1.77 |
| 5 | 295.08 | 388.6 | 1.32 |
| 7 | 180.39 | 224.67 | 1.25 |
| 9 | 129.91 | 158.01 | 1.22 |
| 11 | 101.50 | 121.86 | 1.2 |

The therapeutic ratios resulting from the fixed pulse amplitude process shown in Table 2 indicate a significant increase over the therapeutic ratios resulting from the fixed pulse duration process shown in Table 1. Based on these results, the method of the present invention would select (or recommend) a pulse amplitude of 3 milliamps. with the resulting Therapeutic Ratio of 1.77.

Alternatively, the data in Table 2 may be generated from the data in Table 1. This may be achieved by using the well-known Weiss and/or La Picque formulation and linear estimation techniques for fitting stimulation strength-duration curves. Use of such curve fitting may save time in the clinic by avoiding the need to take more data.

A flow chart of a first embodiment of the method of the present invention is illustrated in FIG. 5. The therapeutic ratios for at least two, and preferably more than two, e.g., five, fixed pulse duration stimulation level control strategies are measured as follows: A fixed pulse duration (width) is selected (block 26) from the at least two, or more, fixed pulses durations. Neurostimulation is then provided (block 28) to the patient at the selected fixed pulse duration (width) and varying pulse amplitudes. The pulse amplitude that corresponds to the pulse amplitude where the stimulation is just perceptible to the patient is recorded (block 30). Next, the pulse amplitude that corresponds to the pulse amplitude at which the maximum comfortable stimulation level is perceived by the patient is recorded (block 32). The therapeutic ratio is then computed (block 34) by dividing the pulse amplitude at the maximum comfortable stimulation level by the pulse amplitude at the just-perceptible stimulation level. A determination is then made as to whether all fixed pulse durations have been tested (block 36). If not, the steps depicted at blocks 26, 28, 30, 32 and 34 are repeated for each fixed pulse duration (width) of the at least two fixed pulse durations Still with reference to FIG. 5, once the therapeutic ratio for all of the at least two fixed pulse durations has been measured, a similar process is executed for a fixed pulse amplitude stimulation level control strategy. That is, a fixed pulse amplitude is selected (block 38) from at least two, and preferably more, e.g., at least five, fixed pulses amplitudes. Neurostimulation is then provided to the patient at the selected fixed pulse amplitude with varying pulse duration (block 40). The pulse duration at which the stimulation is just perceptible to the patient is recorded (block 42). Further, the pulse duration at which the maximum comfortable stimulation level is perceived by the patient is also recorded (block 44). The therapeutic ratio is next computed by dividing the pulse duration at the maximum comfortable stimulation level by the pulse duration at the just-perceptible stimulation level (block 46). A determination is then made as to whether all pulse amplitudes have been tested (block 48). If not, the steps depicted at blocks 38, 40, 42, 44 and 46 are repeated for each fixed pulse amplitude of the at least two fixed pulse amplitudes.

After therapeutic ratios have been determined for all of the at least two fixed pulse durations and all of the at least two fixed pulse amplitudes, the control strategy 50 is selected that provides the greatest therapeutic ratio as the best stimulation control strategy (block 50). The best stimulation control strategy may then either be provided as a recommendation, or may be automatically programmed into the neurostimulation system. If two or more stimulation control strategies offer similar therapeutic ratios, then the stimulation control strategy that offers the least power consumption is selected or recommended. One way of determining at least a component of the power consumption associated with a given stimulation control strategy is to determine the power in each stimulation pulse by multiplying the amplitude of the pulse times the pulse duration (width). Such computation—referred to as obtaining the amplitude-duration (AD) product—is also a useful tool to help determine a stimulation control strategy as described more fully below in connection with FIG. 6.

A flow chart of a second embodiment of the method of the present invention is illustrated in FIG. 6. As seen in FIG. 6, a fixed pulse duration is selected from at least two, or more, e.g., five, fixed pulse durations (block 82). Neurostimulation is then employed that provides stimulation to a patient at the selected fixed pulse duration (block 84), and at varying pulse amplitudes. The pulse amplitude corresponding to the just-perceptible stimulation level is recorded (block 84). Next, the amplitude-duration (AD) product is computed by multiplying the recorded pulse amplitude of the just-perceptible stimulation level times the corresponding fixed pulse duration (block 88). The pulse amplitude associated with the maximum comfortable stimulation level is also recorded (block 90). The AD product is again computed by multiplying the recorded pulse amplitude of the maximum comfortable stimulation level times its corresponding fixed pulse duration (block 92). A determination is then made as to whether all fixed pulse durations of the at least two fixed pulse duration values have been selected (block 94). If not (NO branch of block 94), the steps 82, 84, 86, 88 90 and 92 are repeated until all of the fixed pulse durations have been selected.

When all of the fixed pulse durations have been selected, and corresponding AD products have been computed for the pulse amplitudes associated with the just-perceptible and maximum-comfortable stimulation levels for each selected pulse duration (YES branch of block 94), then a stimulation level control strategy is selected based on the AD products that have been computed (block 96). More particularly, the pulse amplitude and pulse duration that offers the smallest lower AD product may be selected as the minimum stimulation parameters, and the pulse amplitude and pulse duration associated with the greatest upper AD product may be selected as the maximum stimulation parameters. As needed, a stimulation level trajectory between the minimum stimulation parameters and the maximum stimulation parameters may be estimated by interpolating results obtained for pulse durations between the pulse duration associated with the minimum stimulation parameters and the maximum stimulation parameters. Additional measurements may be taken to obtain sufficient data for a smooth interpolation, if necessary. Alternatively, a curve fitting method may be used to fit a smooth trajectory to the measurements.

Those skilled in the art will recognize that the second embodiment described in connection with FIG. 6 may be readily adapted or revised to a method which uses a first step of selecting a fixed pulse amplitude from a plurality of fixed pulse amplitudes, and thereafter varies the pulse duration to determine the just perceptible and maximum comfortable stimulation levels. Such variations of the method depicted in FIG. 6, and variations incorporating other stimulation parameters, are intended to come within the scope of the invention.

As has been indicated, each of the embodiments of the present invention may result in multiple solutions with similar performance. In the such case, the power required by each solution may be compared, and the solution with the least power requirement selected.

Those skilled in the art will recognize that various adjustments and modifications may be made to the method of the present invention. Moreover, those of skill in the art, given the descriptions presented herein, will also be able to fashion numerous detailed approaches for achieving the high-level steps, or equivalent steps, shown in FIG. 5 or FIG. 6, in order to carry out the invention. Typically, the invention will be carried out using a processor-based neural stimulator system, e.g., of the type disclosed in the previously-referenced U.S. Pat. No. 6,516,27, with appropriate control of the stimulator system being provided through software or firmware code coupled to or embedded within the processor. Alternatively, appropriate logic circuitry, e.g., state control logic, may be used by those of skill in the art to implement the processes of the invention. The heart of the present invention relates to providing an improvement to the therapeutic ratio by selecting a stimulation level control strategy (e.g., a particular combination of pulse widths, pulse amplitudes, and pulse rates) that maximizes the effectiveness of the range of the patient controlled stimulation level parameters. Methods which utilize variations to the steps described herein, or methods that apply to stimulation parameters other then those discussed herein, are intended to come within the scope of the present invention. Further, combinations of the methods described herein are intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A method for maximizing the therapeutic ratio (TR) of a neurostimulator system, wherein the therapeutic ratio is defined as the ratio of a maximum comfortable stimulation level (numerator) to a just-perceivable stimulation level (denominator), comprising:

determining the pulse amplitudes of the just-perceptible stimulation level for a patient for at least two fixed pulse durations;

determining the pulse amplitudes of the maximum comfortable stimulation level for the patient for the at least two fixed pulse durations; determining a fixed duration therapeutic ratio for each of the at least two fixed pulse durations;

determining the pulse durations of the just-perceptible stimulation level for the patient for at least two fixed pulse amplitudes;

determining the pulse durations of the maximum comfortable stimulation level for the patient for the at least two fixed pulse amplitudes; determining a fixed amplitude therapeutic ratio for each the at least two fixed pulse amplitudes; and selecting a stimulation level control strategy that maximizes the therapeutic ratio.

2. The method of claim 1 wherein:

determining the pulse amplitudes of the just-perceptible stimulation level for a patient for at least two fixed pulse durations comprises measuring the pulse amplitudes of the just-perceptible stimulation level for a patient for at least two fixed pulse durations;

determining the pulse amplitudes of the maximum comfortable stimulation level for the patient for the at least two fixed pulse durations comprises measuring the pulse amplitudes of the maximum comfortable stimulation level for the patient for the at least two fixed pulse durations;

determining the pulse durations of the just-perceptible stimulation level for the patient for at least two fixed pulse amplitudes comprises measuring the pulse durations of the just-perceptible stimulation level for the patient for at least two fixed pulse amplitudes; and determining the pulse durations of the maximum comfortable stimulation level for the patient for the at least two fixed pulse amplitudes comprises measuring the pulse durations of the maximum comfortable stimulation level for the patient for the at least two fixed pulse amplitudes.

3. The method of claim 1 wherein:
determining the pulse amplitudes of the just-perceptible stimulation level for a patient for at least two fixed pulse durations comprises measuring the pulse amplitudes of the just-perceptible stimulation level for a patient for at least two fixed pulse durations;
determining the pulse amplitudes of the maximum comfortable stimulation level for the patient for the at least two fixed pulse durations comprises measuring the pulse amplitudes of the maximum comfortable stimulation level for the patient for the at least two fixed pulse durations; determining the pulse durations of the just-perceptible stimulation level for the patient for at least two fixed pulse amplitudes comprises applying a curve fitting method to determine the pulse durations of the just-perceptible stimulation level for the patient for at least two fixed pulse amplitudes; and
determining the pulse durations of the maximum comfortable stimulation level for the patient for the at least two fixed pulse amplitudes comprises applying a curve fitting method to determine the pulse durations of the maximum comfortable stimulation level for the patient for the at least two fixed pulse amplitudes.

4. The method of claim 3 wherein the applying a curve fitting method comprises applying a Weiss and/or La Picque formulation.

5. The method of claim 3 wherein applying a curve fitting method comprises applying a Weiss and/or La Picque formulation.

6. The method of claim 1 wherein:
determining the pulse amplitudes of the just-perceptible stimulation level for a patient for at least two fixed pulse durations comprises applying a curve fitting method to determine the pulse amplitudes of the just-perceptible stimulation level for a patient for at least two fixed pulse durations;
determining the pulse amplitudes of the maximum comfortable stimulation level for the patient for the at least two fixed pulse durations comprises applying a curve fitting method to determine the pulse amplitudes of the maximum comfortable stimulation level for the patient for the at least two fixed pulse durations;
determining the pulse durations of the just-perceptible stimulation level for the patient for at least two fixed pulse amplitudes comprises measuring the pulse durations of the just-perceptible stimulation level for the patient for at least two fixed pulse amplitudes; and
determining the pulse durations of the maximum comfortable stimulation level for the patient for the at least two fixed pulse amplitudes comprises measuring the pulse durations of the maximum comfortable stimulation level for the patient for the at least two fixed pulse amplitudes.

7. The method of claim 1 wherein selecting a stimulation level control strategy that maximizes the therapeutic ratio comprises:
selecting a largest therapeutic ratio as the largest of the set consisting of the fixed duration therapeutic ratios and the fixed amplitude therapeutic ratios;
wherein if the largest therapeutic ratio results from one of the at least two fixed pulse amplitudes:
selecting a fixed parameter to be the one of the at least two fixed pulse amplitudes resulting in the largest therapeutic ratio; and
selecting a variable parameter to be the pulse duration; and
wherein if the largest therapeutic ratio resulted from one of the at least two fixed pulse durations
selecting the fixed parameter to be the one of the at least two fixed pulse durations resulting in the largest therapeutic ratio; and
selecting the variable parameter to be the pulse amplitude; and
selecting a stimulation level control strategy that includes the fixed parameter and the variable parameter.

8. The method of claim 7 wherein selecting a stimulation level control strategy further comprises providing the selected fixed parameter and the selected variable parameter as recommended stimulation parameters.

9. The method of claim 7 wherein selecting a stimulation level control strategy further comprises automatically providing the selected fixed parameter and the selected variable parameter to the neurostimulator system for use as stimulation parameters.

10. The method of claim 7 wherein selecting a largest therapeutic ratio comprises:
selecting a largest therapeutic ratio as the largest of the set consisting of the fixed duration therapeutic ratios and the fixed amplitude therapeutic ratios; and
wherein if two or more of the set consisting of the fixed duration therapeutic ratios and the fixed amplitude therapeutic ratios have approximately the same largest value, selecting the largest therapeutic ratio which results in the smallest current drain on a power source of the system.

11. The method of claim 1 wherein the at least two fixed pulse durations comprise at least five fixed pulse durations, and wherein the at least two fixed pulse amplitudes comprise at least five fixed pulse amplitudes.

12. The method of claim 1 wherein the neurostimulator system comprises a Spinal Cord Stimulation (SCS) system.

13. An implantable neural stimulation system comprising:
an electrode array;
an Implantable Pulse Generator (IPG);
an electrical connection between the IPG and the electrode array; and
means for controlling the IPG based on a stimulation strategy that produces a large Therapeutic Ratio (TR) wherein the therapeutic ratio is defined as the ratio of a maximum comfortable stimulation level to a just-perceivable stimulation level.

14. The system of claim 13 wherein the means for controlling the IPG so as to provide a large TR comprises means for determining a stimulation level control strategy that maximizes the TR by selecting one of a fixed pulse duration control strategy and a fixed pulse amplitude control strategy as a function of which results in the largest TR.

15. A method for maximizing the therapeutic ratio (TR) of a neurostimulator system, comprising:
(a) selecting one of at least two fixed pulse durations;
(b) performing the following steps:
(1) providing neurostimulation to a patient at the selected fixed pulse duration and with a varying pulse amplitude,
(2) computing a lower amplitude-duration (AD) product as the product of the selected fixed stimulation duration and the stimulation amplitude at the just-perceptible stimulation level, and (3) computing an upper AD product as the product of the selected fixed stimulation duration and the stimulation amplitude at the maximum comfortable stimulation level;

(c) selecting a new one of the at least two fixed pulse durations and repeating steps (b)(1) through (b)(3) for the newly selected fixed pulse duration;

(d) selecting the one of the at least two fixed pulse durations which resulted in the smallest lower AD product and the pulse amplitude that resulted in the smallest lower AD product as the minimum stimulation level;

(e) selecting the one of the at least two fixed pulse durations which resulted in the greatest upper AD product and the pulse amplitude that resulted in the greatest upper AD product as the maximum stimulation level; and (f) creating a stimulation level control strategy that runs from the minimum stimulation level to the maximum stimulation level.

16. The method of claim 15 wherein creating a stimulation level control strategy that runs from the minimum stimulation level to the maximum stimulation level comprises:

measuring at least one just-perceptible stimulation level and at least one maximum comfortable stimulation level for at least one intermediate pulse duration between the pulse duration of the minimum stimulation level and the pulse duration of the maximum stimulation level; and interpolating at least one intermediate pulse amplitude between the pulse amplitude of the just-perceptible stimulation level and the pulse amplitude of the maximum comfortable stimulation level; and fitting curves between the minimum stimulation level and at least one intermediate stimulation level at the at least one intermediate pulse duration, and between the at least one intermediate stimulation level and the maximum stimulation level.

* * * * *